US00PP14054P39

(12) United States Plant Patent
Snoeijer

(10) Patent No.: US PP14,054 P3
(45) Date of Patent: Aug. 12, 2003

(54) CLEMATIS PLANT NAMED 'ZOIN'

(76) Inventor: Wim Snoeijer, Vest 162, 2801 TX, Gouda (NL)

( * ) Notice: Subject to any disclaimer, the term of this patent is extended or adjusted under 35 U.S.C. 154(b) by 10 days.

(21) Appl. No.: 09/956,455

(22) Filed: Sep. 19, 2001

(65) Prior Publication Data

US 2003/0056257 P1 Mar. 20, 2003

(51) Int. Cl.[7] ..... A01H 5/00
(52) U.S. Cl. ..... Plt./228
(58) Field of Search ..... Plt./228

(56) References Cited

PUBLICATIONS

UPOV ROM GTITM Computer Database, GTI JOUVE retreival software 2002/02, citation for 'Zoin'.*

* cited by examiner

*Primary Examiner*—Bruce R. Campell
*Assistant Examiner*—W C Haas

(57) ABSTRACT

A new cultivar of Clematis named 'Zoin' that is characterized by an upright scandent habit, low to medium height and pink flowers that are suitable for use as cut flowers. In combination these traits set 'Zoin' apart from all other existing varieties of Clematis known to the inventor.

2 Drawing Sheets

Botanical Classifciation: *Clematis diversifolia.*
Variety denomination: 'Zoin'.

BACKGROUND OF THE INVENTION

The present invention relates to a new and distinct cultivar of Clematis, a woody half climber that is grown for use in small gardens and for its cut flowers. The new cultivar is known botanically as a *Clematis diversifolia* and will be referred to hereinafter by the cultivar name 'Zoin'.

'Zoin' was bred by the inventor in 1993 in a cultivated area of Boskoop, Netherlands by crossing the female parent *Clematis integrifolia* 'Rosea' (not patented) with the male parent Clematis 'Warsawska Nike' (not patented). The breeder's goal was to produce a pink form of Clematis 'Durandii'. In addition, the breeder sought to produce a low-growing clematis resistant to disease and wilt that produces long lasting cut flowers. Only one cross was made. There were no intermediate crosses. 'Zoin' was selected by the inventor in 1997 from the many resulting seedlings. Its pink flower with contrasting yellow stamens is a unique to the diversifolia group.

The distinguishing characteristics of 'Zoin' are its upright habit, pink bell shaped flowers, long flowering, low to medium height and blossoms that are suitable for use as cut flowers. The closest comparison plant is *Clematis durandii* (unpatented) which exhibits a blue flower. 'Zoin' is distinguishable from *Clematis durandii* by its pink colored flowers.

'Zoin' was first asexually propagated by the inventor in Boskoop, Netherlands in 1998 using softwood cuttings. Since that time, under careful observation, the distinguishing characteristics have been determined stable and uniform in successive generations.

SUMMARY OF THE INVENTION

The following represent the distinguishing characteristics of the new Clematis cultivar 'Zoin'. In combination these traits set 'Zoin' apart from all other existing varieties of Clematis known to the inventor. 'Zoin' has not been tested under all possible conditions and phenotypic differences may be observed with variations in environmental, climatic, and cultural conditions, however, without any variance in genotype.

1. The flowers of Clematis 'Zoin' are suitable for use as cut flowers.
2. Clematis 'Zoin' is low to medium in height and suitable for a small garden.
3. Clematis 'Zoin' exhibits bell shaped pink flowers in spring and summer.
4. Clematis 'Zoin' is a woody half climber that is hardy to USDA Zone 5.
5. Clematis 'Zoin' exhibits dark green foliage.
6. Clematis 'Zoin' is resistant to wilt and disease.
7. Clematis 'Zoin' exhibits an upright habit.

BRIEF DESCRIPTION OF THE DRAWINGS

The accompanying color photographs illustrate the distinguishing traits of the new Clematis cultivar 'Zoin'. The plants in the photographs were grown out of doors in Boskoop, Netherlands in one-gallon containers before planting in the ground.

The first drawing illustrates entire plants in bloom from a side perspective.

The second drawing is a close-up view of the leaves and flowers. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Clematis cultivar named 'Zoin.' Data was collected in Arroyo Grande, Calif. from the inventor and plants grown in one-gallon containers out of doors. Color determinations are in accordance with The Royal Horticultural Society Colour Chart except where general color terms of ordinary dictionary significance are used. The growing requirements are similar to the species. Under normal growing conditions there are no known disease problems known to the inventor.

Botanical classification: *Clematis diversifolia* 'Zoin'.
Common name: Virgins bower.
Uses: Cut flowers and climber for a small garden.
Parent: 'Zoin' is a hybrid resulting from the induced hybridization of the following plants:
*Female parent.*—*Clematis integrifolia* 'Rosea'.
*Male parent.*—Clematis 'Warsawska Nike'.
Type: Perennial.
Vigour: Vigorous. Generally grows 1.70 meters in length during the first year.
Habit: Upright and scandent.
Height (one-gallon): 42 cm. in height (at maturity 'Zoin' is 150–200 cm. in height).
Width (one-gallon): 60 cm. in width.
Hardiness: USDA Zone 5.
Disease resistance: Resistant to clematis wilt.
Propagation: Softwood cuttings.
Root system: Fibrous.
Soil: Plant in well-drained soils.
Sunlight: Plant in full sunlight.
Plant sexuality: Bisexual.
Time to initiate roots: 2 weeks are required for an initial cutting to produce roots.
Crop time: 8–10 months are required to produce a finished one-gallon from a rooted cutting.
Seasonal interest: Flowers in spring and summer.
Stem:
*Branching habit.*—Upright.
*Internode length.*—8–10 cm. between nodes.
*Stem diameter.*—3 mm. in diameter.
*Stem length.*—40 cm. in length.
*Shape.*—Cylindrical and articulate.
*Surface.*—Fluted with pubescent nodes.
*Stem color.*—171B.
Foliage:
*Type.*—Deciduous.
*Leaf arrangement.*—Opposite.
*Leaf division.*—Compound (singular and ternary).
*Leaflet division.*—Simple.
*Leaflet shape.*—Oblong to lanceolate.
*Leaflet base.*—Base of terminal leaflet obtuse-subcordate. Base of side leaves oblique.
*Leaflet apex.*—Attenuate.
*Leaflet venation.*—Reticulate.
*Vein color* (*adaxial surface*).—147D.
*Vein color* (*abaxial surface*).—147D.
*Leaf surface* (*adaxial*).—Matte and puberulent.
*Leaf surface* (*abaxial*).—Shiny and puberulent.
*Leaf attachment.*—Petiolate and articulate. Side leaflets are subsessile to short articulate.
*Petiole dimensions.*—2.5–6 cm. in length and 2 mm. in diameter.
*Petiole color.*—138C.
*Petiole shape.*—Cylindrical and twisted.
*Leaf margin.*—Entire and revolute.
*Leaf texture.*—Soft and flexible.
*Leaf length.*—7–9 cm. in length.
*Leaf width.*—5–7 cm. in width.
*Leaflet length.*—2–4 cm. in length.
*Leaflet width.*—1–2 cm. in width.
*Leaf color* (*adaxial surface*).—147A.
*Leaf color* (*abaxial surface*).—147C.
*Foliar fragrance.*—Absent.
Flower:
*Flower form.*—Solitary, axillary and terminal inflorescence.
*Inflorescence type.*—Dichasial cyme.
*Persistent or self-cleaning.*—Self-cleaning.
*Color of peduncle.*—148D.
*Peduncle length.*—5.1–10 cm. in length.
*Peduncle diameter.*—1.1–3 mm. in diameter.
*Surface of peduncle.*—Pubescent.
*Diameter of flower.*—6–10 cm. in diameter.
*Shape.*—Open campanulate.
*Sexuality.*—Bisexual.
*Aspect.*—Facing upwards.
*Bud.*—Upright and lanceolate.
*Bud color.*—61A.
*Bud surface.*—Glossy.
*Petals.*—Apetalous.
*Tepals.*—Four in number.
*Color of tepals* (*inside surface*).—A combination of 72C suffused with 67A.
*Color of tepals* (*outside surface*).—72C.
*Tepal shape.*—Oblanceolate — obovate.
*Tepal apex.*—Revolute and mucronate.
*Tepal surface.*—Furrowed.
*Tepal margin.*—Sinuous and pubescent.
*Tepal length.*—5 cm. in length.
*Tepal width.*—3 cm. in width.
*Unfused or fused.*—Tepals are unfused and do not overlap.
*Blooming period.*—End of June, July, August and the beginning of September.
*Fragrance.*—Slightly fragrant.
Reproduction organs:
*Stamens.*—Polyandrous.
*Pubescence.*—Present.
*Arrangement of stamens.*—Spirally arranged.
*Color of stamen filament.*—12B.
*Dimensions of stamen.*—0.5–0.8 cm. in length and 1 mm in diameter.
*Dimensions of anther.*—1 mm. in width and 0.4 cm. in length.
*Pollen color.*—4D.
*Anther color.*—4D to 151A and becoming black 202A.
*Pistil.*—One.
*Color of pistil.*—155C.
*Dimensions of pistil.*—0.9–1 cm.
*Pubescence.*—Present.
*Stigma color.*—155C.
*Style color.*—155C.
*Style form.*—Plumose.
*Style dimensions.*—2 cm. in length and 3–4 mm. in width.
*Ovary position.*—Superior.
*Ovary color.*—Pale brown.
*Ovary shape.*—Oval.
Seed:
*Dimensions of fruit.*—4 cm. in diameter and 2 cm. in height.
*Seed surface.*—Villous.
*Villi color.*—156C.
*Seed shape.*—Oval.
*Seed color.*—136A.
*Seed dimensions.*—1.50 mm. in diameter and 3 mm. in length.

I claim:

1. A new and distinct variety of Clematis plant named 'Zoin' as described and illustrated.

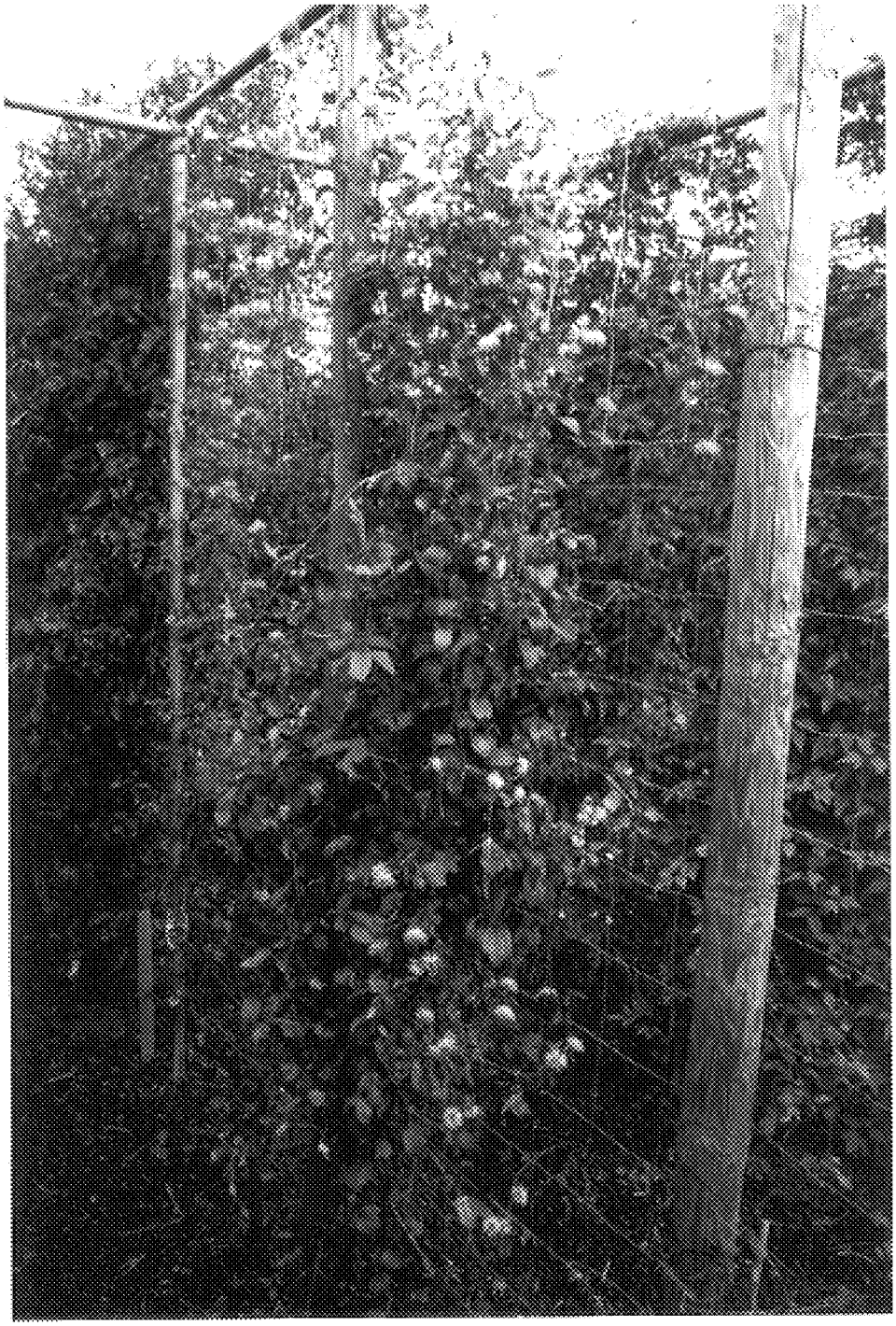

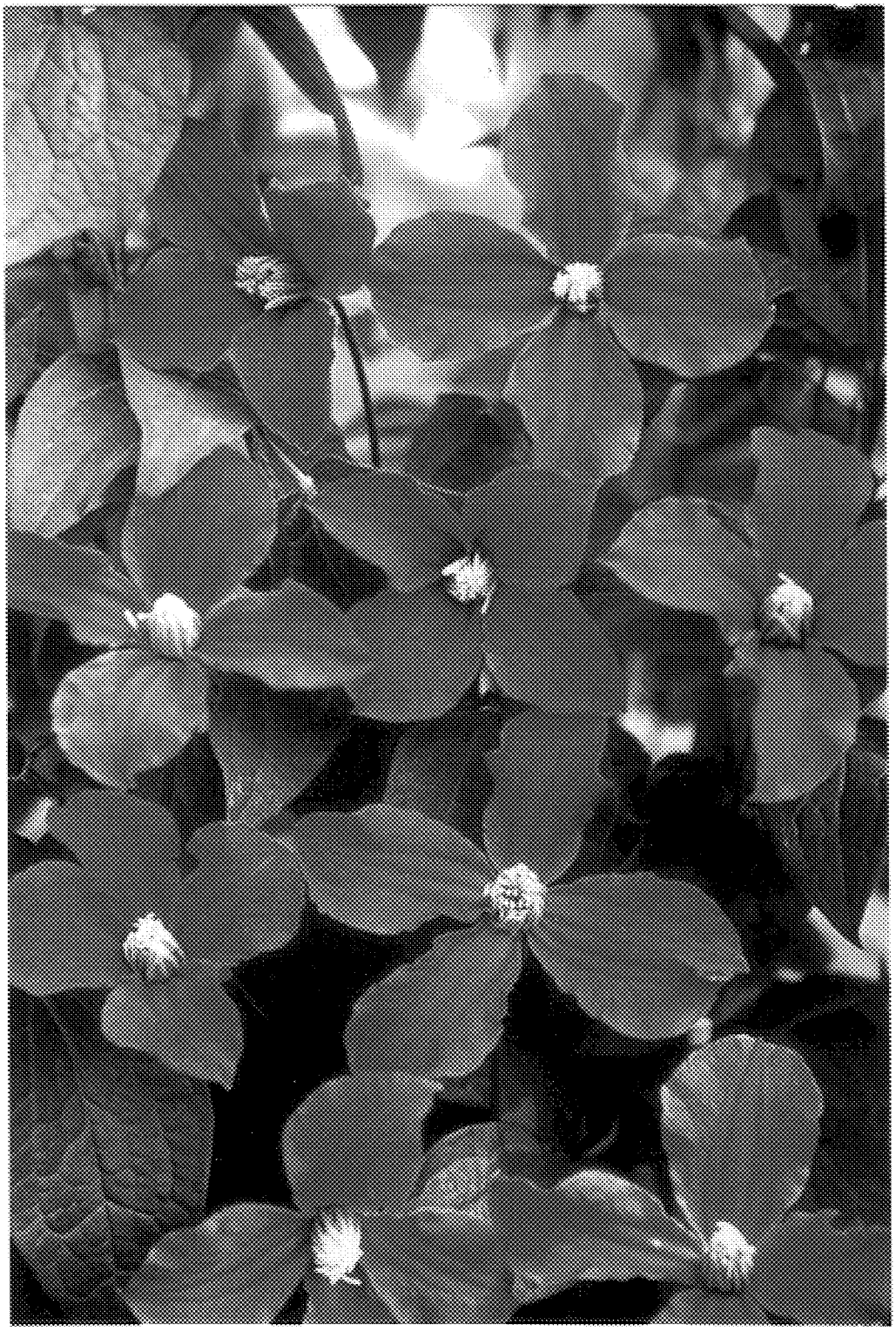

* * * * *